United States Patent [19]

Scherrmann et al.

[11] Patent Number: 5,817,770
[45] Date of Patent: Oct. 6, 1998

[54] COCAETHYLENE IMMUNOGENS AND ANTIBODIES

[75] Inventors: Jean-Michel Scherrmann, Enghien Les Bains, France; Philippe Pouletty, Atherton, Calif.; Herve Galons, Paris, France

[73] Assignee: Drug Abuse Sciences, Inc., Hillsborough, Calif.

[21] Appl. No.: 821,895

[22] Filed: Mar. 21, 1997

[51] Int. Cl.[6] .......................... C07K 16/00; A61K 38/00; C07D 451/02
[52] U.S. Cl. ...................... 530/389.8; 530/345; 530/363; 435/188; 436/543; 436/547; 540/130
[58] Field of Search ..................................... 530/345, 363, 530/389.8, 806; 435/186, 961; 436/543, 547, 816, 823; 546/130

[56] References Cited

U.S. PATENT DOCUMENTS 5,202,270  4/1993  Ungemach et al. ................. 530/389.8

FOREIGN PATENT DOCUMENTS

WO 93/12111  6/1993  WIPO .

OTHER PUBLICATIONS

Jonathan Oyler et al., Journal of Analytical Toxicology, vol. 20, pp. 453–462, Oct. 1996.

*Primary Examiner*—Ponnathapura Achutamurthy
*Assistant Examiner*—P. Ponnaluri
*Attorney, Agent, or Firm*—Bertram I. Rowland

[57] ABSTRACT

The ethyl ester of derivatives of benzoyl ecgonine are provided having a linking group at the para position of the benzoyl group. The derivatives are used to bond to immunogenic polypeptides for production of antisera and monoclonal antibodies. The antisera and antibodies find use in assays, for treatment of cocaine overdose and detoxification.

16 Claims, No Drawings

COCAETHYLENE IMMUNOGENS AND ANTIBODIES

INTRODUCTION

Background

Drug addiction remains a scourge of all societies, whether supplier or consumer. The predominant drugs used today are cocaine, heroin and methamphetamine in the order of their usage. There is no present antagonist for cocaine, as there is for heroin. Cocaine acts in an entirely different way from heroin in blocking the channels of the presynaptic neuron for retrieval of dopamine. Therefore, any antagonist must bind to the channel in a way which inhibits cocaine binding, while permitting the channel to retrieve the dopamine from the synaptic space. In the absence of an antagonist, other ways of responding to various hazards associated with cocaine are necessary.

There have been recent reports that a vaccine against cocaine is being developed, which is the subject matter of W096/30049. Also, there has been a report that a compound has been found which binds to the dopamine channel without closing the channel and inhibits the action of cocaine. However, these efforts are in the early stages of development and may never demonstrate efficacy in patients and drug addicts.

Cocaine is known to be rapidly metabolized to benzoylecgonine, which is believed to be physiologically inactive. Furthermore, cocaine becomes rapidly distributed in the various compartments of the body and can provide a rush in less than a minute, depending upon the method of administration. It is known that if one imbibes alcohol when taking cocaine, there is a rapid transesterification to the ethyl ester called "cocaethylene." Cocaethylene is known to retain efficacy longer.

In the absence of a specific antagonist, the treatment for cocaine overdose is to sedate the patient and provide drugs to ameliorate the bradycardia. Therefore, during the time that it is important for the doctor to communicate with the patient, the patient is comatose. Since cocaine appears to be able to distribute itself rapidly into different compartments, the ability to remove the cocaine from the blood, should also result in reducing the amount of cocaine in the brain and heart. However, there are uncertainties with the use of antibodies to sequester cocaine in the blood as part of the treatment of cocaine overdose, in that antibodies have a much larger molecular weight than cocaine and the amount of antibody required for efficacy could be prohibitive, both physiologically and economically, the therapeutic response is uncertain, the average dose of cocaine in the case of overdose is not known and the antibodies should be able to bind to whatever active compound is present in the blood, while not binding to physiologically inactive compounds.

SUMMARY OF THE INVENTION

Novel compositions are provided based on the ethyl ester of benzoylecgonine or its amide analog. Linking groups are bonded to the benzoyl group for conjugation to a T cell epitope for immunization of mammals for the production of antisera which specifically binds to cocaine and cocaethylene, while having a low affinity to benzoylecgonine. The B cells from the mammalian host may be used to produce monoclonal antibodies having the same specificity spectrum. The antisera and monoclonal antibodies may be used in assays for intact cocaine and cocaethylene, for treatment of cocaine overdose, in cocaine detoxification, vaccination and in other applications associated with cocaine and its ethyl analog.

DESCRIPTION OF THE SPECIFIC EMBODIMENTS

In accordance with the subject invention compositions are provided which have the N-methylated tropane structure and are derivatives of the ethyl ester analog. The compounds find use as intermediates to the production of immunogens or as the immunogens. In addition, the antisera and monoclonal antibodies derived therefrom find use in the treatment of cocaine addiction and cocaine overdose, in assays for cocaine and the ethyl analog and other applications associated with cocaine.

For the most part, the compounds are the ethyl ester of benzoyl ecgonine, or the amino analogs thereof, where one or both of the oxy groups is replaced with nitrogen, having a linking group bonded at the para position to the benzoyl group, which linking group terminates in a carboxyl group. The linking group will generally have from 1 to 10, more usually 1 to 6, atoms, where up to 4, more usually from 1 to 2 atoms may be heteroatoms, particularly oxygen nitrogen, sulfur and phosphorus. Of interest is to have the heteroatom joined to an annular atom. Generally, the linking group will be aliphatic, usually free of aliphatic unsaturation. When used to bond to the antigenic protein to produce an immunogen, the carboxyl group will be activated for reaction with the protein in an aqueous medium.

For the most part, the compounds of this invention will have the following formula:

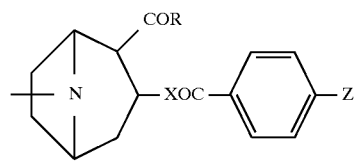

wherein:
R is oxyethyl or aminoethyl:
X is O or NH; and
Z is an aliphatic linking group of from 1 to 10, usually 1 to 6, more usually 1 to 5 atoms, particularly 2 to 6, more particularly 2 to 4, atoms, primarily carbon atoms, and may have from 0 to 4, usually 0 to 2, more usually 1 to 2 heteroatoms, where the heteroatoms will be oxygen, nitrogen, sulfur and phosphorous, particularly oxygen and nitrogen, where the oxygen may be present as oxy or oxo, and the nitrogen will be present as amino and amido; where the linking group may terminate in a carboxy group or derivative thereof (not included in the number of atoms of the linking group), particularly an activated carboxy group, e.g. a group providing for reaction with amino groups in an aqueous medium, mixed anhydride, e.g. carbodiimide, activated ester, or the like, or a T cell epitope, normally a polypeptide of at least about 5 kD. A wide variety of polypeptides have found use as immunogens to produce antibodies to haptens, where the hapten is conjugated to the immunogen, usually multiply conjugated.

For the linking group, various groups may be employed, such as ethylenecarboxyl, butylenecarboxyl, oxyacetyl, oxypropionyl, oxysuberyl, oxyethyloxyacetyl, aminoacetyl, aminobutyryl, aminocaproyl and the like.

Various polypeptides may be employed for the cocaethylene immunogen. Polypeptides which find use include bovine serum albumin, keyhole limpet hemocyanin, cholera toxin B, hepatitis B surface antigen, γ-globulin, tetanus toxoid, or other protein which the host to be immunized may or may not have been previously exposed. The immunogen will normally be at least about 5 kD and may be 1 or more million kD. There will be at least one compound conjugated and up to about 1 per 10 kD.

The cocaethylene hapten may be conjugated to the immunogen in accordance with conventional ways. The carboxyl group is activated with an activating agent which allows for amide formation with the immunogen in an aqueous environment. Depending on the size and nature of the immunogen, one may use an amount of cocaethylene hapten 0.1 to 10 times the available number of amino groups. Usually, one will not use more than 5 times the available number of amino groups to minimize cost. The immunogen and activated cocaethylene derivative are brought together in an appropriately buffered aqueous medium and usually allowed to react under mild conditions, <50° C., and with agitation, for sufficient time for the reaction to go to completion. The immunogen product may then be isolated by conventional means and purified using gel electrophoresis, chromatography, affinity chromatography and the like. The immunogen composition may be analyzed for the average number of cocaethylene molecules per immunogen molecule.

To produce antibodies, an appropriate mammalian host may be used, such as murine, lagomorpha, ovine, bovine, canine, feline, equine, primate, including humans, and the like. The immunogen is injected into the host at an appropriate site, e.g. subcutaneously, intramuscularly, intraperitoneally, intravenously, and the like. The immunogen is formulated, usually with an adjuvant, such as complete Freund's adjuvant, alum, various complex lipid-sugar membrane oligomers, or the like. After the initial injection, usually one or more booster injections will be given at periods of from 2 to 4 weeks, until the desired titer and affinity have been achieved. Booster shots may then be continued, as appropriate, to maintain the titer and affinity and to continue to provide antisera. The same or different adjuvant may be used in successive injections and the same or different immunogen may be used in successive injections. The amount of immunogen used will vary depending on the host, the host's response to the immunogen, the manner in which the immunogen is administered, the cost of the immunogen, and the like. The amount of immunogen employed will generally be in the range of about 0.5 to 10 mg/kg.

After each injection, usually waiting at least 3 days, the plasma will be analyzed for antisera for cocaethylene and the titer and affinity determined for cocaine and its metabolites. Titers of at least 1:20,000 are desirable, preferably at least 1:50,000. The affinity for cocaine and cocaethylene should not differ by more than 2 fold, while the affinity for benzoylecgonine should be at least 5 fold less, preferably at least 10 fold less than the lesser affinity for cocaine and cocaethylene. The antibodies should be IgG primarily or the equivalent in the particular host. Affinities for cocaine and/or cocaethylene will usually be at least about $5 \times 10^{-8}$, generally ranging up to about $10^{-11}$, usually in the range of about $10^{-9}$ to $10^{-10}$.

When using antisera, the antisera may be harvested in conventional ways, depending upon the host. The antisera may be precipitated with ammonium sulfate and then subjected to further enrichment using chromatography, electrophoresis, and the like, to provide for a composition comprising primarily IgG.

For use in a human host, the antisera should be thoroughly purified to remove impurities which may initiate an immune response, other than the mild immune response anticipated from antisera obtained, for example, from ovine or equine sources. The antisera will be formulated in accordance with known procedures and with known components, depending upon the manner in which it is administered. For intravenous use, the antisera will usually be dissolved in an appropriate physiologically acceptable medium with physiologically acceptable additives, such as phosphate buffered saline, saline, aqueous glucose, etc. For injection, similar media may be employed. The antisera concentration will generally be in the range of about 10 to 50 weight percent of the solution, where an injection will generally have from about 0.5 to 3 g of the antisera.

The antisera may be used for treatment of humans suffering from cocaine overdose, where the antisera will bind to cocaine and cocaethylene in the plasma and reduce their effective concentration in the plasma, thus reducing their concentration in the brain and heart. The antisera may also be used in detoxification for cocaine and as an aid in rehabilitation of a cocaine addict. The antisera may also play a role in the treatment of cocaine dementia.

In order to prepare monoclonal antibodies, B cells are isolated, usually from the spleen (splenocytes) of the immunized host and immortalized in conventional ways, e.g. fusion with a myeloid cell, transfection with a transforming virus, or the like. The resulting immortalized cells are cloned and the antibodies from the different clones screened for their specificity and affinity. The hybridoma cells producing desired antibodies are expanded and may be used for the production of monoclonal antibodies. The monoclonal antibodies are isolated and purified in accordance with conventional ways.

The monoclonal antibodies may be used in substantially the same way as the antisera, but are less likely to be found satisfactory for chronic use and they may produce an immune effect specific for the antibody idiotype.

The antisera and monoclonal antibodies may be used in immunoassays for the detection of cocaine and cocaethylene in physiological fluids of humans or other mammalian hosts, such as blood, urine, saliva, cerebrospinal fluid and the like. Numerous immunoassays are known and are commercially available, such as ELISA, EMIT, SLIFIA, etc., where these assays may be adapted for use with the subject antibodies. Conveniently, competitive assays may be employed where cocaine and/or cocaethylene are bound to a surface, for example, by conjugation to a protein bound to a surface and any drug in the blood can compete for the antibodies with the drug bound to the surface. By employing labeled antibodies, where the label provides for the production of a detectable signal, e.g. radioactivity, fluorescence, light absorption, etc., the amount of the drug in the blood can be quantitated. By using the antibodies of the subject invention one can better determine whether a patient has been taking both cocaine and alcohol and the longer lasting cocaethylene is present in the physiological fluid. Since the affinity for the antisera or the monoclonal antibody can be different for cocaine and cocaethylene, by using a plurality of different combinations of cocaine and cocaethylene, one can determine the relative amount of cocaine and cocaethylene in the physiological fluid.

EXPERIMENTAL

The NMR spectra were recorded on a Bruker 270 MHz spectrophotometer. Column chromatography was performed using silica gel (60–200 μm). Eluent A:

Benzene:CH$_2$Cl$_2$:AcOEt 8:1:1; Eluent B: CH$_2$Cl$_2$:AcOEt:NEt$_3$ 80:20:1

Ecgonine Ethyl Ester Hydrochloride.

Ecgonine hydrochloride (4.4 g, 20 mmol) obtained by complete hydrolysis of cocaine by refluxing in dilute HCl was suspended in 50 ml of ethanol cooled at 0° C. Thionyl chloride (1 ml, 12 mmol) was added dropwise. After the addition was complete, the mixture was refluxed overnight, filtered hot to remove any unreacted ecgonine hydrochloride and evaporated to dryness. This product was used without purification. Yield 81% (crude product)

Preparation of 4-(benzyloxyaceatebenzaldehyde,

A mixture of potassium tert.-butoxide (11.2 g, 100 mmol), 4-hydroxybenzaldehyde (12.2 g, 100 mmol), Aliquat 336 (0.5 g) and toluene (5 ml) was vigorously stirred at room temperature for 15 min. A solution of benzyl bromoacetate (16 ml) in toluene (20 ml) was added dropwise in 10 min. The mixture was heated at 70° C. with stirring for 3 h and then cooled to room temperature. Water was added and the product extracted with CH$_2$Cl$_2$ (3×20 ml)and purified by chromatography using Eluent A. Rf=0.4

Preparation of 4-(benzyloxyacetate benzoic acid.

To a cooled (0° C.) solution of 4-(benzyloxyacetate) benzaldehyde in CH$_2$Cl$_2$ was added 6 ml of a solution of CrO$_3$ (3.85 g in 10 ml H$_2$O and 3.2 ml H$_2$SO$_4$). After 30 min stirring, methanol (5 ml) was added slowly and the mixture poured on ice (20 g) and extracted with CH$_2$Cl$_2$ (3×20 ml) and purified by crystallization from isopropanol and drying in vacuo over P$_2$O$_5$.

Preparation of 4-(benzyloxyacetateobenzoyl chloride

To a suspension of 4-(benzyloxyacetate)benzoic acid in CH$_2$Cl$_2$ (5 ml) is added thionyl chloride in 0.1 ml dimethylformamide. The mixture is refluxed for 15 min and evaporated to dryness. Anhydrous toluene (5 ml) was added and the solution evaporated to dryness. The resulting solid was further dried for 15 min in vacuo (30° C., 0.5 mm Hg) to completely remove any thionyl chloride. The product was used directly without further purification.

Preparation of the ethyl ester of O-(2"-benzylacetate) 4'-hydroxybenzoylecgonine.

To ethyl ecgonine hydrochloride (2.5 g, 10 mmol) in 10 ml cooled (5° C.) toluene:CH$_2$Cl$_2$ (1:1) was added 4-dimethylaminopyridine (1.22 g, 10 mmol) and triethylamine (2.5 ml, 2 mmol) and the mixture stirred for 5 min followed by the addition of 4-(benzyloxyaccetate)benzoyl chloride in CH$_2$Cl$_2$ (5 ml). After stirring for 15 min at 5° C., the mixture was refluxed for 3 h. After cooling to room temperature, water was added and the mixture extracted with CH$_2$Cl$_2$ (3×20 ml). The organic layer was concentrated and purified with column chromatography (Eluent B). Yield: 86%

Preparation of the ethyl ester of O-(acetic acid) 4'-hydroxybenzoylecgonine.

To a solution of the ethyl ester of O-(2"-benzyl acetate) 4'-hydroxybenzoylecgonine in ethanol (50 ml) was added Pd-C 10% and the solution vigorously stirred under hydrogen (atm. pressure). Stirring was continued for an additional 30 min after completion of the absorption of hydrogen (total reaction time of about 1.5 h) and the solution filtered over Micropore filter. The product was isolated by evaporation of the solution.

Synthesis of cocaethylene-immunocogulates a.) The ethyl ester of O-acetic acid) 4'-hydroxybenzoylecgonine (50 mg) (hapten) was dissolved in 2 ml of dioxane. 2×25 µl of tri-n-butylamine were added. 1 The mixture was cooled to 4° C. and then 26 µl of isobutylchloroformate were added. The mixture was stirred at 4° C. for 20 min. The mixture was added to a solution of BSA or keyhole limpet hemocyanin (KLH) (120 mg dissolved in 6 ml of 1/1 water/dioxane). The reaction mixture was stirred for 4 h. The pH was controlled and adjusted between 7.5 and 8.5 during the 4 h with 1N NaOH. At the end of the 4 h, the solution was dialysed against PBS, pH 7.4 for 2 days. The number of moles of the hapten was determined by the TNBS method. The immunoconjugate was collected and stored at −80° C.

b.) TNBS titrations were carried out by adding to 0.5 ml of a BSA or conjugate solution (1 mg/ml) in a glass vial, 1 ml of 4% sodium carbonate and 1 ml of a 0.1% TNBS solution. The vials were incubated 2 h at 37° C. in a water bath and then 1 ml of a 10% SDS solution added, followed by 0.5 ml of 1M HCl. UV absorbance was measured at 342 nm (a sample which contained 0.5 ml of water was used as a blank). Each sample was tested in triplicate and the results were averaged. The calculated percent of hapten bound to BSA was derived from the extent of BSA free amine.

c.) Specifically to a solution of hapten (391 mg, 1 mmol) in dioxane 5 mL is added 0.5 mL of triehylamine. The solution is cooled to 10° C. and isobutylchloroformate (155 µL, 1.2 mmol) is added. The mixture is stirred at room temperature during 30 mn.

This solution is added during 2 mn time to a solution of 700 mg of BSA, at pH=8, in water 10 mL. The mixture is stirred 4 h at room temperature. During the stirring, the pH is measured and adjusted at 8 by addition of small amounts of 0.1N sodium hydroxide. The TNBS method indicated about 15 molecules of hapten per BSA.

Immunization of mice and rabbits with the above conjugate.

Either of the following protocols were used for the immunization of mice:

a) Balb/c mice were immunized with 100 µg (200 µl) for the conjugate in Freund's complete adjuvant by intraperitoneal route during 4 weeks with a boost each week. After 4 weeks, mice were immunized in the same way as the other method.

b) Balb/c mice were immunized with 100 µg (200 µl) of the antigen in Freund's complete adjuvant by subcutaneous route at the base of the tail every two weeks.

In each case, control groups were performed with the unconjugated protein.

The antisera obtained from the immunizations performed in the above examples were characterized as to affinity and competition with benzoyl ecgonine and cocaethylene. The assay employed was an RIA assay performed as follows:

[$^3$H]- Cocaine, 28.5 Ci/mol, was purchased from New England Nuclear (Paris, France). Cocaine, benzoylecgonine and cocaethylene were purchased from Sigma-Aldrich (La Perpillière, France). Aqualyte scintillation liquid was from Packard (Rungis, France) and all chemical reagents of analytical purity from Merck (Nogent sur Marne, France).

1. Titration of cocaine-specific antibodies.

Antibody titers were performed using the RIA procedure. 100 µl of various antisera dilutions were added to 50 µl of phosphate-buffered saline (PBS), pH 7.4, 50 µl of free plasma and 300 µl of [$^3$H]-cocaine (20000 dpm) (tracer) in disposable polypropylene tubes. Determination of the total radioactivity (AT), the non-specific binding of the tracer (AT-NS) were included. After mixing and incubation for 2 h at room temperature, the fraction of cocaine bound to the antibodies was separated from the unbound fraction by addition of 500 µl of a saturated ammonium sulfate solution. After incubation for 15 min and centrifugation at 4000 t/min at 4° C., 500 µl of the supernatant was decanted into 3 ml of scintillation liquid. Radioactivity of the free fraction was counted in a Tricarb 1900 TR β-counter (Packard, Rungis, France). results were expressed as percentage of free cocaine (F/AT-NS) versus antibody dilutions, where F=free cocaine. The curve was fitted by using the GraphPad program (ISI, CA). The titer is defined as the dilution of anti-cocaine antisera which gives 50% of [$^3$H]-cocaine binding.

2. Specificity of cocaine-specific antibodies.

Specificity of antibodies was determined by testing the cross-reactivity of structural analogs (benzoylecgonine (BE)) and cocaethylene (CocaE) according to the RIA procedure. Cross-reactivity was expressed as the percentage ration of cocaine concentration to the cross-reacting structural analogs (inhibition) concentration at 50% inhibition of maximum binding. 100 μl of antisera at the dilution which gave 50% of [$^3$H]-cocaine binding were added to 50 μl of structural analogs of cocaine (BE and CocaE) with 300 μl of [$^3$H]-cocaine (20000 cpm). The affinity constant of cocaine antiserum was calculated according to the method of M üller (R. Müller. Calculation of average antibody affinity in anti-hapten sera from data obtained by competitive radio-immunoassay. Journal of Immunological Methods, 34, 345–352 (1980)).

The following table indicates the results:

| Immunogen | Rabbit | Titer | Affinity ($M^{-1}$) RIA ×10$^8$ | Specificity (%) RIA BE | Specificity (%) RIA CocaE |
|---|---|---|---|---|---|
| 1 | A | 395 | 6.2 | 5 | 53 |
|   | B | 449 | 2.9 | 7 | >100 |
|   | C | 767 | 5.8 | — | 60 |
| 2 | D | 48  | 2.0 | 11 | 67 |
|   | E | 147 | 2.2 | 17 | >100 |
|   | F | 589 | 5.2 | 18 | >100 |
| 3 | G | 382 | 8.5 | — | >100 |
|   | H | 100 | 16  | — | >100 |
|   | I | 900 | 90  | 9 | >100 |

1. BSA conjugate.
2. KLH conjugate.
3. KLH conjugate.

It is evident from the above results that the subject immunogens provide for effective detection and neutralization of both cocaine and its metabolite cocaethylene, while having low or negligible binding to benzoyl ecgonine. In addition, the subject immunogens provide for high titers and high affinities, particularly as repetitive booster shots are employed, where it was previously found with other immunogens, that high cross-reactivity to benzoyl ecgonine was observed as the booster shots progressed.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. N-methyl tropane substituted at the 2-position by carboxyethyl or N-ethylcarboxamnide and at the 3-position by benzoyloxy or benzamido, wherein bonded at the para position of said benzoyloxy or benzamido is a linking group or a carboxy group, and when said linking group is present, a carboxy group is attached to said linking group, wherein at least one of the substituents has an amido group.

2. A compound according to claim 1, wherein said linking group is of 1 to 6 atoms.

3. A compound according to claim 1, wherein said linking group is attached to said benzoyl group through an oxygen atom.

4. A compound according to claim 3, wherein said linking group is of 1 to 6 atoms.

5. A compound according to claim 1, wherein said carboxyl group is joined to a functional group to react with a protein in an aqueous medium.

6. An immunogen comprising the ethyl ester of benzoyl ecgonine and an antigenic protein, said antigenic protein is linked to the benzoyl group of the ethyl ester of benzoyl ecgonine through a carboxyl group at the para position.

7. An immunogen according to claim 6, wherein said antigenic protein is bovine serum albumin.

8. An immunogen according to claim 6, wherein said antigenic protein is keyhole limpet hemocyanin.

9. A method for producing antisera which have a high affinity of at least 5×10$^{-8}$ for cocaine and cocaethylene and a low affinity for benzoyl ecgonine, said method comprising:

immunizing a mammal with an immunogen according to claim 6 with at least one booster shot, wherein antisera is produced with a high affinity for cocaine and cocaethylene and a low affinity for benzoyl ecgonine.

10. Antisera produced according to the method of claim 9.

11. Antisera according to claim 10, wherein said mammal is a rabbit.

12. Antisera according to claim 10, wherein said mammal is a horse.

13. A compound of the formula N-methyl 2-carboxyethyl-3-benzoyloxytropane, where the benzoyloxy group at the para position is substituted with a linking group, and a carboxy group is attached to said linking group.

14. A compound according to claim 13, where said linking group is of one to six atoms.

15. A compound according to claim 13, wherein said carboxy group is an activated carboxy group capable of reacting with a protein in an aqueous medium.

16. An immunogen comprising N-methyl 2-carboxyethy-3-benzoyloxytropane bonded to an antigenic protein, wherein said benzoyloxy group at the para position is substituted with a linking group and a carboxy group is attached to said linking group, said antigenic protein is linked to said carboxy group.

* * * * *